United States Patent [19]

Ogawa et al.

[11] 4,148,822

[45] Apr. 10, 1979

[54] PROCESS FOR THE MANUFACTURE OF METHACRYLIC OR ACRYLIC ACID

[75] Inventors: Masanobu Ogawa; Toshitake Kojima, both of Takasaki, Japan

[73] Assignee: Nippon Kayaku Kabushiki Kaisha, Tokyo, Japan

[21] Appl. No.: 646,375

[22] Filed: Jan. 2, 1976

[30] Foreign Application Priority Data

Jan. 16, 1975 [JP] Japan .................................. 50-6233

[51] Int. Cl.$^2$ ........................ C07C 51/32; C07C 57/04
[52] U.S. Cl. .................................. 562/534; 252/435; 252/437; 562/536
[58] Field of Search .................... 260/530 N; 562/534

[56] References Cited

U.S. PATENT DOCUMENTS

| 3,646,127 | 2/1972 | Akiyama et al. | 260/530 N |
| 4,042,623 | 8/1977 | Ogawa | 260/530 N |

FOREIGN PATENT DOCUMENTS 1362068  7/1974  United Kingdom ............... 260/530 N Primary Examiner—Vivian Garner
Attorney, Agent, or Firm—Russell & Nields

[57] ABSTRACT

Methacrolein or acrolein is oxidized with molecular oxygen in the presence of water vapor, a catalyst containing palladium, phosphorus, antimony(optionally) and oxygen and a phosphoric acid or a compound capable of forming phosphoric acid during the reaction.

9 Claims, No Drawings

PROCESS FOR THE MANUFACTURE OF METHACRYLIC OR ACRYLIC ACID

BACKGROUND OF THE INVENTION

This invention relates to a process for the production of methacrylic or acrylic acid by oxidizing methacrolein or acrolein.

More particularly, this invention relates to a process for the production of methacrylic or acrylic acid by oxidizing methacrolein or acrolein with molecular oxygen in the presence of water vapor characterized in that the reaction system is provided with a catalyst which contains palladium, phosphorus and oxygen as essential elements and antimony as an optional element and that a phosphoric acid or a phosphorus compound capable of forming a phosphoric acid through a chemical change during the reaction is concurrently supplied to the reaction system.

For the synthesis of methacrylic acid by oxidizing methacrolein in vapor phase a number of catalysts have hitherto been proposed.

Almost all of these catalysts, however, have low catalytic activities. Further, if the reaction is carried out at elevated temperatures in order to increase the total rate of reaction, these catalysts are degraded or decomposed at such elevated temperatures to yield large amounts of undesirable by-products such as carbon monoxide, carbon dioxide, etc. so that the per-pass yield of methacrylic acid is very low.

The catalyst as disclosed in the Japanese Patent Laid-open Publication Nos. 67216/1973 and 61416/1973, which are improved in their catalytic activity and selectivity, comprise phosphomolybdic acid or salts thereof as a main ingredient.

The phosphomolybdic catalyst has serious disadvantages that it is short in its service life and thermally unstable so that the catalytic activity starts to rapidly decrease at a reaction or calcination temperature of more than 450° C. Once the catalyst has been deteriorated, it can be regenerated no more by a simple treatment, for example, by calcining it again. These facts show that the phosphomolybdic catalyst is not always available for commercial use.

Further, when the reaction is to be carried out at high space velocities, the service life of the phosphomolybdic catalyst will considerably be reduced.

From a commercial aspect, it is desired to develop a catalyst which has acceptable activity and selectivity at low temperatures as well as a longer service life. Particularly desirable is a catalyst which can maintain its activity over a long period of time even when the reaction is carried out at high speed velocities.

DESCRIPTION OF THE INVENTION

The inventors have made a study on the manufacture of methacrylic and acrylic acids, particularly on a catalyst suitable for their manufacture and the influence thereon, in order to obviate the above-described disadvantage of the prior art and have found a process for the production of methacrylic or acrylic acid from methacrolein or acrolein wherein not only the conversion of methacrolein or acrolein is high, but also the selectivity of methacrylic or acrylic acid produced is high at low temperatures and a novel catalyst therefor which has a longer service life even under the condition of a high space velocity.

According to the present invention, not only methacrolein or acrolein is susceptible to oxidation at low temperatures and methacrylic or acrylic acid is produced in high yields, but also the formation of by-products such as acetic acid, carbon monoxide and carbon dioxide owing to the degradation is well suppressed. In addition the catalyst according to the present invention has a substantially longer service life, particularly even when the reaction is carried out at high space velocities.

The catalyst to be used in the present invention is a composition consisting of palladium, phosphorus and oxygen as essential elements and antimony as an optional element and has a long service life which is significantly superior to that of the prior phosphomolybdic catalyst.

It was found that the catalyst used herein is stable at elevated temperatures, for example, at 600° C.

However, this catalyst as such is not completely satisfactory, because a part of phosphorus which is one of the essential components of the catalyst, though in a very small amount, leaves out of the catalyst system during the reaction. Consequently, the semi-eternal life required for commercial catalysts can not be attained.

The inventors have found that when the reaction is carried out in the presence of the catalyst, the catalyst can be stabilized and its service life can further be prolonged by continuously or intermittently supplementing phosphorus in an appropriate amount corresponding to that of the phosphorus which leaves out of the catalyst system.

The process of the present invention is epoch-making and of great value for commercial use since methacrylic or acrylic acid can be selectively produced in high yields for long periods of time.

The term "a phosphoric acid or a phosphorus compound capable of forming a phosphoric acid through a chemical change during the reaction" (hereinafter to be referred to as a phosphorus-containing compound) which is to be supplied to the reaction system in accordance with the present invention means any phosphoric acids and phosphorus compounds capable of forming a phosphoric acid through a chemical reaction such as hydrolysis, oxidation, etc., including orthophosphoric acid, pyrophosphoric acid, metaphosphoric acid, phosphoric acid, hypophosphorous acid, phosphine, organic phosphoric acids, solid phosphoric acids, etc.

To the reaction system the phosphorus-containing compound may be supplied in any suitable manner.

For example, if the phosphorus-containing compound is water-soluble, it may uniformly be dissolved in water to be used for the reaction so that it is carried to the reaction system along with water.

If the phosphorus-containing compound is solid, for example, a solid phosphoric acid, this solid material may be charged in front of the catalyst layer. As water vapor is fed and made contact with the charged material, the latter generates a phosphoric acid, which is carried to the catalyst layer along with water vapor.

Furthermore, if the phosphorus-containing compound is gaseous, a gaseous mixture of the same and air may be fed to the catalyst layer.

An amount of the phosphorus-containing compound to be supplied may vary over a wide range. In general, the phosphorus-containing compound is supplied so that the amount of phosphorus contained in the compound is preferably 5 to $1 \times 10^{-4}$ wt.%, more particularly 0.5 to $1 \times 10^{-3}$ wt.% on the basis of a total amount of water fed during the reaction.

A preferred catalyst according to the present invention is a composition represented by the following formula:

$$Pd_aP_bSb_cO_d$$

in which suffices a, b, c, and d represent numbers of palladium, phosphorus, antimony and oxygen atoms, respectively, preferably when a is 1, b is 1 to 42, c is 0 to 15, and d is a number which is of itself deermined by total valences of other elements, generally from 3.5 to 115.

A more preferred catalyst is a composition represented by the above formula in which the ratio among a, b, c and d lies in the following range:

$$a:b:c:d = 1:(1-28):(0.2-10):(3.8-85)$$

The catalyst according to the present invention can be prepared in a convention manner well known in the art, for example, by the following procedures.

In one case, compounds of respective constituent elements and the carrier, if a carrier is used, are mixed. The resultant solution is evaporated to dryness and then the dried product is calcined.

In another case, a solid carrier is impregnated with compounds of respective constituent elements. This impregnated carrier is evaporated to dryness and then calcined.

In yet another case, a solid carrier is impregnated with compounds of some constituent elements and then subjected to a heat treatment, preferably at a temperature of 100°–800° C. The partly impregnated carrier is further impregnated with compounds of the remaining constituent elements. This twice impregnated carrier is evaporated to dryness and then calcined.

In any of the above-described procedures the calcination temperature lies preferably in a range of 300°–800° C., more preferably in a range of 350°–550° C.

Examples of compounds of respective constituent elements are listed below.

Specific examples of palladium compounds include palladium chloride, nitrate and sulfate, palladium black and the like.

Specific examples of phosphorus compounds include orthophosphoric, pyrophosphoric, metaphosphoric, polyphosphoric, phosphorous and hypophosphorous acids and salts thereof and the like.

Specific examples of antimony compounds include oxides, hydroxides and chlorides of antimony such as antimony trioxide, trichloride and pentachloride and the like.

It is preferred to use a carrier for the catalyst, because the carrier makes it possible to lower the concentration of the catalyst, enhance the catalytic action and achieve catalyst economy.

As the carrier may be employed inert substances such as silica sol, silica gel, silicon carbide, α-alumina, Alundum, celite, boiling bubble stone, aluminum powder and the like.

Molecular oxygen is used for oxidizing methacrolein or acrolein in accordance with the present invention. To this end air is generally used. Pure oxygen may also be used alone or in admixture with an inert gas such as nitrogen, carbon dioxide and the like.

To the reaction system methacrolein or acrolein and oxygen are fed as a gaseous feed mixture in such proportions that the molar ratio of methacrolein or acrolein to oxygen is preferably 1:(0.5–30), more preferably 1:(1–8).

The reaction between methacrolein or acrolein and oxygen is carried out in the presence of water vapor according to the process of the present invention. The presence of water vapor is indispensable to this reaction. If water vapor is absent, the oxidation of methacrolein or acrolein may occur to a very small extent or may not occur at all. In this aspect the catalyst according to the present invention is virtually different from known catalysts used for the oxidation of methacrolein or acrolein.

The water vapor is involved in the gaseous feed mixture in such proportions that the amount of water vapor is preferably 0.5 to 40 moles, more preferably 1 to 28 moles per mole of methacrolein or acrolein.

The temperature for carrying out the reaction is not so critical. The reaction may preferably be carried out at a temperature of 180° to 420° C., especially 210° to 390° C.

The reaction can be carried out at atmospheric pressure or at lower or higher pressures. In general it is convenient to carry out the reaction at atmospheric pressure. A preferable range of pressure is 0.3 to 15 atm.

The gaseous feed mixture can be introduced at any desirable space velocity, preferably at a space velocity of 300 to 15,000 l-gas/l-cat.hr, especially 700 to 8,000 l-gas/l-cat.hr.

According to the present invention satisfactory results are obtained even when the reaction is carried out at space velocities as high as 2,000 to 8,000 l-gas/l-cat.hr. Further the service life of the catalyst is maintained for a long period of time under such conditions.

The catalyst of the present invention may be applied in any form selected from a fixed bed, a fluidized bed and a moving bed.

The following examples are illustrative of the catalyst and the process of the present invention. In the examples, the terms "conversion of methacrolein or acrolein", "selectivity of methacrylic or acrylic acid", "yield of methacrylic or acrylic acid", and "space velocity" are defined as follows.

Conversion of methacrolein or acrolein = 
$$\frac{\text{A number of moles of the reacted methacrolein or acrolein}}{\text{A number of moles of the fed methacrolein or acrolein}} \times 100$$

Selectivity of methacrylic or acrylic acid =
$$\frac{\text{A number of moles of the produced methacrylic or acrylic acid}}{\text{A number of moles of the reacted methacrolein or acrolein}} \times 100$$

Yield of methacrylic or acrylic acid =
$$\frac{\text{A number of moles of the produced methacrylic or acrylic acid}}{\text{A number of moles of the fed methacrolein or acrolein}} \times 100$$

Space Velocity (SV) =
$$\frac{\text{A flow rate* of a gaseous feed mixture (l-gas/hr)}}{\text{A volume of a charged catalyst (l-cat.)}}$$
*calculated on a basis at the normal temperature and pressure.

EXAMPLE 1

With heating and stirring to 115.8 g of silica sol was added 0.71 g of antimony trioxide. This mixture was heated to concentrate the same, evaporated to dryness and then dried at 270° C. for eight hours. The dried product was impregnated with aqueous ammonia containing 0.9 g of palladium chloride and then evaporated to dryness. After the dried product was repeatedly washed with distilled water (the total amount is 10 l) and dried, it was further impregnated with 5.4 g of hypophosphorous acid, evaporated to dryness and then dried at 270° C. for another eight hours. The dried product was calcined in the air at 450° C. for four hours. The thus obtained product is named Catalyst A, the composition of which is represented by the formula:

$$Pd_1P_5Sb_1O_{15}$$

A reaction tube of stainless steel having an inner diameter of 20 mm was filled with 10 ml of Catalyst A and dipped in a bath of molten nitrate. With the use of this reaction tube filled with Catalyst A the oxidation of methacrolein was carried out for 120 days.

As the phosphorus-containing compound was used orthophosphoric acid in the form of a 0.05% aqueous solution.

A gaseous feed mixture contained methacrolein, oxygen, water vapor, nitrogen and phosphorus in a relative molar ratio of $1:4:14:16.1:9\times10^{-4}$.

The results are shown in Table 2. On the production of methacrylic acid from methacrolein small amounts of by-products were derived, in which were included 2.0% of acrylic acid, 1.3% of acetic acid, 5.1% of carbon dioxide and 6.0% of carbon monoxide.

EXAMPLE 2

Example 1 was repeated except that solid phosphoric acid (celite/phosphorus=50/50) heat treated at 550° C. was used as the phosphorus-containing compound in place of orthophosphoric acid.

On the upper side of the catalyst layer consisting of 10 ml of Catalyst A was placed 5 ml of the solid phosphoric acid.

The results are shown in Table 2.

EXAMPLE 3

Example 1 was repeated except that trimethyl phosphate in the form of a 0.05% aqueous solution was used as the phosphorus-containing compound in place of orthophosphoric acid.

The relative molar ratio between methacrolein, oxygen, water vapor, nitrogen and phosphorus in the gaseous feed mixture is the same as that of Example 1.

The results are shown in Table 2.

EXAMPLES 4–8

Catalysts B-F each consisting of the composition shown in Table 1 were prepared in accordance with the procedures described in Example 1, respectively. With the use of these catalysts Example 3 was repeated. The results are shown in Table 2.

EXAMPLE 9

Silica sol (115.8 g) was concentrated with heating and stirring, evaporated to dryness and then dried at 270° C. for eight hours. The dried product was impregnated with aqueous ammonia containing 0.9 g of palladium chloride and then evaporated to dryness. After the dried product was repeatedly washed with distilled water (a total amount is 10 l) and dried, it was further impregnated with 5.4 g of hypophosphorous acid, evaporated to dryness and then dried at 270° C. for another eight hours. The dried product was calcined in the air at 450° C. for four hours. The thus obtained product is named Catalyst G, the composition of which is represented by the formula:

$$Pd_1P_5O_{13.5}$$

With the use of Catalyst G the oxidation of methacrolein was carried out in a similar manner as in Example 1. The results are shown in Table 2.

On the production of methacrylic acid from methacrolein at a space velocity (SV) of 1,500 hr$^{-1}$ small amounts of by-products including 2.7% of acrylic acid, 1.5% of acetic acid, 6.1% of carbon dioxide and 7.2% of carbon monoxide were derived.

EXAMPLES 10–13

Catalysts H-K each consisting of the composition shown in Table 1 were prepared in accordance with the procedures described in Example 9. With the use of these catalysts Example 3 was repeated. The results are shown in Table 2.

Table 1

| Example | Pd (a) | P (b) | Sb (c) | O (d) | |
|---|---|---|---|---|---|
| 1-3 | 1 | 5 | 1 | 15 | Catalyst A |
| 4 | 1 | 1 | 0.5 | 4.25 | Catalyst B |
| 5 | 1 | 10 | 1 | 27.5 | Catalyst C |
| 6 | 1 | 15 | 1 | 40 | Catalyst D |
| 7 | 1 | 20 | 2.5 | 54.75 | Catalyst E |
| 8 | 1 | 5 | 7 | 24 | Catalyst F |
| 9 | 1 | 5 | — | 13.5 | Catalyst G |
| 10 | 1 | 1 | — | 3.5 | Catalyst H |
| 11 | 1 | 2 | — | 6 | Catalyst I |
| 12 | 1 | 10 | — | 26 | Catalyst J |
| 13 | 1 | 15 | — | 38.5 | Catalyst K |

Table 2

Production of Methacrylic acid from Methacrolein

| Example | Catalyst | time (day) | SV (hr$^{-1}$) | Temperature nitrate bath (° C.) | Conversion methacrolein (%) | Yield of acid (%) | Selectivity of acid (%) |
|---|---|---|---|---|---|---|---|
| 1 | A | 0 | 1500 | 300 | 77.4 | 61.5 | 79.5 |
|   |   | 40 | 1500 | 300 | 77.0 | 61.7 | 80.1 |
|   |   | 120 | 1500 | 300 | 77.8 | 62.1 | 79.8 |
| 2 | A | 0 | 1500 | 303 | 76.8 | 60.5 | 78.8 |
|   |   | 40 | 1500 | 303 | 75.9 | 61.0 | 80.4 |
|   |   | 120 | 1500 | 303 | 76.4 | 61.3 | 80.2 |
| 3 | A | 0 | 1500 | 300 | 77.8 | 61.9 | 79.6 |
|   |   | 40 | 1500 | 300 | 77.5 | 62.2 | 80.3 |
|   |   | 120 | 1500 | 300 | 77.6 | 62.3 | 80.3 |
|   |   | 0 | 4000 | 309 | 68.5 | 53.9 | 78.7 |
|   |   | 40 | 4000 | 309 | 68.5 | 53.7 | 78.4 |
|   |   | 120 | 4000 | 309 | 68.6 | 54.0 | 78.7 |
| 4 | B | 0 | 1500 | 290 | 82.0 | 53.8 | 65.6 |
|   |   | 0 | 4000 | 301 | 72.5 | 46.3 | 63.9 |
|   |   | 40 | 4000 | 301 | 72.4 | 46.4 | 64.1 |

Table 2-continued

| | | | | Production of Methacrylic acid from Methacrolein | | | |
|---|---|---|---|---|---|---|---|
| Example | Catalyst | time (day) | SV (hr$^{-1}$) | Temperature nitrate bath (° C.) | Conver- methacrolein (%) | Yield of acid (%) | Selectivity of acid (%) |
| | | 120 | 4000 | 301 | 72.4 | 46.5 | 64.2 |
| 5 | C | 0 | 1500 | 306 | 74.3 | 57.1 | 76.9 |
| | | 0 | 4000 | 312 | 65.2 | 48.6 | 74.5 |
| | | 40 | 4000 | 312 | 65.1 | 48.7 | 74.8 |
| | | 120 | 4000 | 312 | 65.3 | 48.7 | 74.6 |
| 6 | D | 0 | 1500 | 311 | 74.0 | 56.2 | 75.9 |
| | | 0 | 4000 | 318 | 64.7 | 46.7 | 72.2 |
| | | 40 | 4000 | 318 | 64.7 | 46.5 | 71.9 |
| | | 120 | 4000 | 318 | 64.8 | 46.7 | 72.1 |
| 7 | E | 0 | 1500 | 317 | 72.7 | 54.2 | 74.6 |
| | | 0 | 4000 | 323 | 62.3 | 45.1 | 72.4 |
| 7 | E | 40 | 4000 | 323 | 62.1 | 44.9 | 72.3 |
| | | 120 | 4000 | 323 | 62.3 | 45.2 | 72.6 |
| 8 | F | 0 | 1500 | 302 | 71.5 | 53.5 | 74.8 |
| | | 0 | 4000 | 320 | 68.5 | 44.1 | 64.4 |
| | | 40 | 4000 | 320 | 68.4 | 44.1 | 64.5 |
| | | 120 | 4000 | 320 | 68.5 | 44.2 | 64.5 |
| 9 | G | 0 | 1500 | 305 | 78.5 | 58.5 | 74.5 |
| | | 40 | 1500 | 305 | 78.9 | 57.9 | 73.4 |
| | | 120 | 1500 | 305 | 78.1 | 58.4 | 74.8 |
| | | 0 | 4000 | 311 | 69.3 | 50.1 | 72.3 |
| | | 40 | 4000 | 311 | 69.2 | 49.9 | 72.1 |
| | | 120 | 4000 | 311 | 69.2 | 50.0 | 72.3 |
| 10 | H | 0 | 1500 | 291 | 81.5 | 52.3 | 64.6 |
| | | 0 | 4000 | 300 | 71.3 | 45.5 | 64.1 |
| | | 40 | 4000 | 300 | 71.3 | 44.8 | 62.8 |
| 10 | H | 120 | 4000 | 300 | 71.4 | 45.1 | 63.2 |
| 11 | I | 0 | 1500 | 296 | 79.1 | 54.7 | 69.2 |
| | | 0 | 4000 | 305 | 70.0 | 47.7 | 68.1 |
| | | 40 | 4000 | 305 | 69.9 | 47.6 | 68.1 |
| | | 120 | 4000 | 305 | 70.1 | 47.8 | 68.2 |
| 12 | J | 0 | 1500 | 311 | 76.5 | 56.1 | 73.3 |
| | | 0 | 4000 | 317 | 67.1 | 47.1 | 70.2 |
| | | 40 | 4000 | 317 | 67.2 | 47.2 | 70.2 |
| | | 120 | 4000 | 317 | 67.1 | 47.1 | 70.2 |
| 13 | K | 0 | 1500 | 315 | 71.1 | 50.1 | 70.5 |
| | | 0 | 4000 | 323 | 60.4 | 41.3 | 68.4 |
| | | 40 | 4000 | 323 | 60.5 | 41.2 | 68.1 |
| | | 120 | 4000 | 323 | 60.7 | 41.4 | 68.2 |

EXAMPLES 14–24

Example 3 was repeated except that acrolein was used in place of methacrolein. As a catalyst Catalysts A–K were used, respectively. The results are shown in Table 3.

Table 3

| | | | | Production of Acrylic Acid from Acrolein | | | |
|---|---|---|---|---|---|---|---|
| Example | Catalyst | Reaction time (day) | SV (hr$^{-1}$) | Temperature of the nitrate bath (° C.) | Conver- sion of acrolein (%) | Yield of acrylic acid (%) | Selectivity of acrylic acid (%) |
| 14 | A | 0 | 1500 | 300 | 96.3 | 91.1 | 94.6 |
| | | 40 | 1500 | 300 | 95.7 | 90.9 | 95.0 |
| | | 120 | 1500 | 300 | 96.5 | 91.3 | 94.6 |
| | | 0 | 4000 | 309 | 91.0 | 83.0 | 91.2 |
| | | 40 | 4000 | 309 | 91.2 | 83.1 | 91.1 |
| | | 120 | 4000 | 309 | 91.1 | 83.2 | 91.3 |
| 15 | B | 0 | 1500 | 295 | 96.5 | 78.1 | 80.9 |
| | | 0 | 4000 | 301 | 90.3 | 69.1 | 76.5 |
| | | 40 | 4000 | 301 | 90.4 | 69.3 | 76.7 |
| | | 120 | 4000 | 301 | 90.2 | 69.0 | 76.5 |
| 16 | C | 0 | 1500 | 304 | 94.0 | 88.1 | 93.7 |
| | | 0 | 4000 | 310 | 89.3 | 80.0 | 89.5 |
| | | 40 | 4000 | 310 | 89.5 | 80.2 | 89.6 |
| 16 | C | 120 | 4000 | 310 | 89.3 | 80.2 | 89.8 |
| 17 | D | 0 | 1500 | 305 | 92.1 | 86.2 | 93.6 |
| | | 0 | 4000 | 312 | 86.4 | 76.4 | 88.4 |
| | | 40 | 4000 | 312 | 86.4 | 76.2 | 88.2 |
| | | 120 | 4000 | 312 | 86.5 | 76.5 | 88.5 |
| 18 | E | 0 | 1500 | 310 | 89.5 | 80.1 | 89.5 |
| | | 0 | 4000 | 319 | 82.1 | 71.0 | 86.5 |
| | | 40 | 4000 | 319 | 82.0 | 71.3 | 87.0 |
| | | 120 | 4000 | 319 | 82.0 | 70.9 | 86.5 |
| 19 | F | 0 | 1500 | 303 | 93.0 | 80.3 | 86.3 |
| | | 0 | 4000 | 312 | 88.5 | 72.1 | 81.4 |
| | | 40 | 4000 | 312 | 88.2 | 72.1 | 81.7 |

Table 3-continued

| | | | | Production of Acrylic Acid from Acrolein | | | |
|---|---|---|---|---|---|---|---|
| Example | Catalyst | Reaction time (day) | SV (hr$^{-1}$) | Temperature of the nitrate bath (° C.) | Conversion of acrolein (%) | Yield of acrylic acid (%) | Selectivity of acrylic acid (%) |
| | | 120 | 4000 | 312 | 88.5 | 72.6 | 82.0 |
| 20 | G | 0 | 1500 | 298 | 93.9 | 80.3 | 85.5 |
| | | 0 | 4000 | 306 | 89.0 | 74.5 | 83.7 |
| 20 | G | 40 | 4000 | 306 | 89.1 | 74.5 | 83.6 |
| | | 120 | 4000 | 306 | 89.1 | 74.7 | 83.8 |
| 21 | H | 0 | 1500 | 94.8 | 75.3 | 79.4 | |
| | | 0 | 4000 | 297 | 89.3 | 67.7 | 75.8 |
| | | 40 | 4000 | 297 | 89.2 | 67.7 | 75.9 |
| | | 120 | 4000 | 297 | 89.2 | 67.6 | 75.8 |
| 22 | I | 0 | 1500 | 295 | 94.4 | 78.1 | 82.7 |
| | | 0 | 4000 | 301 | 89.1 | 71.7 | 80.5 |
| | | 40 | 4000 | 301 | 89.3 | 71.8 | 80.4 |
| | | 120 | 4000 | 301 | 89.1 | 71.8 | 80.6 |
| 23 | J | 0 | 1500 | 302 | 93.1 | 78.2 | 84.0 |
| | | 0 | 4000 | 310 | 88.9 | 72.0 | 81.0 |
| | | 40 | 4000 | 310 | 88.7 | 72.0 | 81.2 |
| | | 120 | 4000 | 310 | 89.0 | 72.1 | 81.0 |
| 24 | K | 0 | 1500 | 306 | 92.1 | 77.0 | 83.6 |
| 24 | K | 0 | 4000 | 314 | 86.4 | 69.9 | 80.9 |
| | | 40 | 4000 | 314 | 86.5 | 70.0 | 80.9 |
| | | 120 | 4000 | 314 | 86.4 | 70.1 | 81.1 |

EXAMPLE 25

Examples 4–8 and 10–24 were repeated except that orthophosphoric acid, metaphosphoric acid, pyrophosphoric acid and solid phosphoric acid were used as the phosphorus-containing compound in place of trimethyl phosphate, respectively, in each case. It has been found that the results are comparable to those of Examples 4–8 and 10–24.

EXAMPLE 26

Examples 1–25 were repeated except that the amount of the phosphorus-containing compound supplied was changed. It has been found that the results are comparable to those of Examples 1–25.

COMPARATIVE EXAMPLES 1–3

(1) In accordance with the procedure of Example 3 described in the Japanese Patent Laid-Open Publication No. 61416/1973 a catalyst in which an atomic ratio of Mo, P, Tl and Si is 1:0.08:0.16:0.08 was prepared. In 400 ml of water was dissolved 237 g of phosphomolybdic acid with slight warming. Besides, to 200 ml of ice water was added dropwise 17.0 g of silicon tetrachloride with stirring. These two solutions were mixed together and heated to a moderate temperature so as to form a homogeneous solution, to which was added another solution of 53.2 g of thallium nitrate in 200 ml of water and then mixed with 50 ml of 28% ammonia water. With stirring the resultant mixture was evaporated to dryness. After the calcination in a muffle furnace at 450° C. for five hours, the product was pulverized into powder, which was molded by means of a tablet machine. Thus obtained tablets were used as a catalyst.

(2) In accordance with the procedure of Example 3 described in the Japanese Patent Laid-open Publication No. 61417/1973 a catalyst in which an atomic ratio of Mo, P, Rb, and Si is 1:0.08:0.16:0.08 was prepared. In 400 ml of water was dissolved 237 g of phosphomolybdic acid with slight warming. Besides, to 200 ml of ice water was added dropwise 17.0 g of silicon tetrachloride with stirring. These two solutions were mixed together and heated to a moderate temperature so as to form a homogeneous solution, to which was added another solution of 29.5 g rubidium nitrate in 200 ml of water and then mixed with 50 ml of 28% ammonia water. With stirring the resultant mixture was evaporated to dryness. After the calcination in a muffle furnace at 450° C. for five hours, the product was pulverized into powder, which was molded by means of a tablet machine. Thus obtained tablets were used as a catalyst.

(3) In accordance with the procedure of Example 1 described in the Japanese Patent Laid-open Publication No. 67216/1973 a catalyst in which an atomic ratio of Mo, P, Cs and Cr is 1:0.16:0.16:0.16 was prepared. In 300 ml of water was dissolved 237 g of phosphomolybdic acid with slight warming. Besides, in 100 ml of water was dissolved 20 g of chromic acid. These two solutions were combined together with stirring. To this mixture were added a solution of 11.5 g of 85% phosphoric acid in 100 ml of water and another solution of 39.0 g of cesium nitrate in 200 ml of warm water. The resultant solution was mixed with 100 ml of 28% ammonia water. With stirring the resultant mixture was evaporated to dryness. After the calcination in a muffle furnace at 450° C. for 16 hours, the product was pulverized into powder, which was molded by means of a tablet machine. Thus obtained tablets were used as a catalyst.

With the use of these three catalysts the oxidation of methacrolein was carried out in accordance with the procedure described in Example 1. In these examples the phosphorus-containing compound was not supplied. The results are shown in Table 4.

Table 4

| Comparative Example | Composition of catalyst | Reaction time (day) | SV (hr$^{-1}$) | Temperature of the nitrate bath (° C.) | Conversion of methacrolein (%) | Yield of methacrylic acid (%) | Selectivity of methacrylic acid (5) |
|---|---|---|---|---|---|---|---|
| 1 | Mo$_1$P$_{0.08}$Tl$_{0.16}$Si$_{0.08}$ | 0 | 4000 | 367 | 70.5 | 51.5 | 73.0 |

Table 4-continued

| Comparative Example | Composition of catalyst | Reaction time (day) | SV (hr$^{-1}$) | Temperature of the nitrate bath (°C.) | Conversion of methacrolein (%) | Yield of methacrylic acid (%) | Selectivity of methacrylic acid (5) |
|---|---|---|---|---|---|---|---|
|   |   | 30 | 4000 | 367 | 63.5 | 48.7 | 76.7 |
|   |   | 60 | 4000 | 367 | 48.5 | 32.5 | 67.0 |
|   |   | 90 | 4000 | 367 | 35.5 | 19.8 | 55.8 |
| 2 | Mo$_1$P$_{0.08}$Rb$_{0.16}$Si$_{0.08}$ | 0 | 4000 | 367 | 70.9 | 50.1 | 70.7 |
|   |   | 30 | 4000 | 367 | 62.6 | 47.3 | 75.6 |
|   |   | 60 | 4000 | 367 | 44.5 | 30.5 | 68.5 |
|   |   | 90 | 4000 | 367 | 34.7 | 18.1 | 52.2 |
| 3 | Mo$_1$P$_{0.16}$Cs$_{0.16}$Cr$_{0.16}$ | 0 | 4000 | 358 | 63.5 | 51.5 | 81.1 |
|   |   | 30 | 4000 | 358 | 57.3 | 46.5 | 81.2 |
|   |   | 60 | 4000 | 358 | 39.5 | 30.1 | 76.2 |
|   |   | 90 | 4000 | 358 | 31.3 | 19.2 | 61.3 |

It is apparent from Table 4 that the prior Mo - P catalysts have shorter service lives and their catalytic activities are remarkably lowered when used in the oxidation of methacrolein for longer periods of time.

In contrast to the oxidation with the prior catalysts, the process of the present invention is an improved one because the catalyst maintains its catalysis satisfactorily for a long period of time.

What is claimed is:

1. A process for the production of methacrylic or acrylic acid by oxidizing methacrolein or acrolein with molecular oxygen in the presence of water vapor characterized in that the reaction system is provided with a catalyst which is a composition represented by the following formula:

$$Pd_aP_bSb_cO_d$$

in which suffixes a, b, c and d represent numbers of palladium, phosphorus, antimony and oxygen atoms, respectively, and wherein a is 1, b is 1 to 42, c is 0 to 15, and d is a number which is of itself determined by the total valences of the other elements and that a phosphoric acid or a phosphorus compound capable of forming a phosphoric acid through a chemical change during the reaction is concurrently supplied to the reaction system.

2. The process according to claim 1 wherein a is 1, b is 1 to 28, c is 0.2 to 10, and d is 3.8 to 85.

3. The process according to claim 1 wherein said phosphoric acid is orthophosphoric acid.

4. The process according to claim 1 wherein said phosphoric acid is pyrophosphoric acid.

5. The process according to claim 1 wherein said phosphoric acid is metaphosphoric acid.

6. The process according to claim 1 wherein said phosphorus compound capable of forming a phosphoric acid through a chemical change during the reaction is an organic phosphoric acid.

7. The process according to claim 1 wherein said phosphorus compound capable of forming a phosphoric acid through a chemical change during the reaction is a solid phosphoric acid.

8. The process according to claim 1 wherein methacrolein is oxidized.

9. The process according to claim 1 wherein acrolein is oxidized.